US012758608B2

(12) United States Patent
Joshi et al.

(10) Patent No.: US 12,758,608 B2
(45) Date of Patent: *Oct. 13, 2026

(54) STABLE PARENTERAL DOSAGE FORM OF CETRORELIX ACETATE

(71) Applicant: Sun Pharmaceutical Industries Limited, Mumbai (IN)

(72) Inventors: Jaydip Joshi, Baroda (IN); Rakesh Thummar, Baroda (IN); Sudeep Agrawal, Baroda (IN); Subhas Balaram Bhowmick, Baroda (IN); Arunkumar Yadav, Baroda (IN); Rajamannar Thennati, Baroda (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/814,447

(22) Filed: Mar. 10, 2020

(65) Prior Publication Data

US 2021/0121517 A1 Apr. 29, 2021

(30) Foreign Application Priority Data

Oct. 24, 2019 (IN) ............................ 201921043355

(51) Int. Cl.

| | |
|---|---|
| ***A61K 38/08*** | (2019.01) |
| ***A61K 9/00*** | (2006.01) |
| ***A61K 9/08*** | (2006.01) |
| ***C07K 14/59*** | (2006.01) |
| *A61K 38/00* | (2006.01) |
| *G01N 30/02* | (2006.01) |
| *G01N 30/16* | (2006.01) |

(52) U.S. Cl.

CPC ............ *A61K 38/08* (2013.01); *A61K 9/0029* (2013.01); *A61K 9/08* (2013.01); *C07K 14/59* (2013.01); *A61K 38/00* (2013.01); *G01N 2030/027* (2013.01); *G01N 30/16* (2013.01)

(58) Field of Classification Search

CPC ...... A61K 9/0019; A61K 38/00; A61K 38/08; A61K 47/42; A61K 9/10; A61K 31/167; A61K 31/606; A61K 47/12; A61K 38/09; A61K 9/19; A61K 31/00; A61K 9/145; C07K 2317/76; C07K 7/06

See application file for complete search history.

(56) References Cited

U.S. PATENT DOCUMENTS

| | | | |
|---|---|---|---|
| 5,773,032 A | 6/1998 | Engel et al. | |
| 7,214,662 B2 | 5/2007 | Sarlikiotis et al. | |
| 7,605,121 B2 | 10/2009 | Engel et al. | |
| 7,718,599 B2 | 5/2010 | Bauer et al. | |
| 8,586,062 B2 | 11/2013 | Khopade et al. | |
| 2002/0039996 A1 | 4/2002 | Bauer et al. | |
| 2003/0216302 A1* | 11/2003 | Bhowmick ............ | A61K 47/18 514/10.9 |
| 2013/0288968 A1 | 10/2013 | George et al. | |
| 2013/0303464 A1* | 11/2013 | Patel ...................... | A61K 38/09 514/21.6 |
| 2018/0325993 A1 | 11/2018 | Rana et al. | |
| 2022/0153802 A1* | 5/2022 | Joshi ...................... | A61P 15/00 |

FOREIGN PATENT DOCUMENTS

| | | |
|---|---|---|
| CA | 2115943 C | 8/2003 |
| CN | 107312073 A | 11/2017 |
| CN | 107664666 A | 2/2018 |
| CN | 109467591 A | 3/2019 |
| EP | 2662073 A1 | 11/2013 |
| WO | 0187265 A2 | 11/2001 |
| WO | 03045419 A1 | 6/2003 |
| WO | 2015004125 A1 | 1/2015 |
| WO | 2021079339 | 4/2021 |

OTHER PUBLICATIONS

Cetrotide Package Insert. EMD Serono, Inc. Apr. 2008. (Year: 2008).*

Chemistry LibreTexts. 20.1: Relative Reactivity, Structure, and Spectra of Carboxylic and Derivatives. p.1-5. Jul. 10, 2015. (Year: 2015).*

Brown et al. Sample Exercise. Chemistry: The Central Science, Eleventh Edition, Copyright © 2009 by Pearson Education, Inc. p. 1-36. (Year: 2009).*

Carlo Remillion. How would you find the appropriate buffer with given pKa's and a given pH? Socratic Q & A Organic Chemictry. https://socratic.org/questions/how-would-you-find-the-appropriate-buffer-with-given-pka-s-and-a-given-ph, 2016. (Year: 2016).*

European Pharmaceutical Review. Breaking old habits: Moving away from commonly used buffers in pharmaceuticals. https://www.europeanpharmaceuticalreview.com/article/13699/breaking-old-habits-moving-away-from-commonly-used-buffers-in-pharmaceuticals/, Jul. 10, 2012. (Year: 2012).*

Cetrorelix Wikipedia Article, Dec. 2018, 1 page.

International Search Report dated Jan. 12, 2021; International Application No. PCT/IB2020/059988; International Filing Date Oct. 23, 2020; 3 pages.

Written Opinion dated Jan. 12, 2021; International Application No. PCT/IB2020/059988; International Filing Date Oct. 23, 2020; 8 pages.

(Continued)

*Primary Examiner* — Melissa L Fisher
*Assistant Examiner* — Jia-Hai Lee
(74) *Attorney, Agent, or Firm* — Blank Rome LLP

(57) ABSTRACT

The present invention relates to a stable parenteral dosage form with a ready-to-inject sterile stable aqueous solution of Cetrorelix acetate. The invention also relates to an injection device prefilled with the ready-to-inject sterile stable aqueous solution of Cetrorelix acetate. The present invention relates a method of inhibiting premature luteinizing hormone surges in women undergoing controlled ovarian stimulation comprising a stable parenteral dosage form with a ready-to-inject sterile stable aqueous solution of Cetrorelix acetate.

20 Claims, No Drawings

(56) References Cited

OTHER PUBLICATIONS

Taiwanese Examination Report issued in related Taiwan Patent Application No. 109136923 on Jul. 11, 2024 and English Translation.

Ondrugdelivery: "Prefilled Syringes & Injection Devices," Jul. 10, 2019, Issue No. 101, 112 Pages, [Retrieved on Jun. 11, 2024].

Agrawal, et al., "Parenteral Delivery of Peptides and Proteins", Chapter 11, pp. 531-622 of Challenges in Delivery off Therapeutic Genomics and Proteonics, 2011.

Izutsu, Ken-Ichih. , "Stabilization of Therapeutic Proteins by Chemical and Physical Methods", Chapter 22 of Therapeutic Proteins Methods and Products, Ed. by Smales and James, Humana Press, 2005, pp. 287-292.

O'Connor, Charmianh. , "Acidic and Basic Amide Hydrolysis", Q. Rev. Chem. Soc., 1970, 24:553-564.

Reissmann, et al., "The LHRH Antagonist Cetrorelix: A Review", Humana Reproduction, 2000, 6:4:322-331.

Letter Accompanying Subsequently filed Items in European Patent Application No. 3811927, mailed Aug. 26, 2025, 4 Pages.

Extended European Search Report for European Application No. 20162018.4 , dated Sep. 9, 2020, 08 Pages.

PUBCHEM: "Cetrorelix" PubChem CID-25074887, [Retrieved on Oct. 6, 2024], 58 Pages.

International Preliminary Report on Patentability for International Application No. PCT/IB2020/059988, dated May 5, 2022, 10 Pages.

O'Hondt, M. et al., "Related impurities in peptide medicines", Journal of Pharmaceutical and Biomedical Analysis, vol. 101, No. C, pp. 2-30, 2014.

* cited by examiner

STABLE PARENTERAL DOSAGE FORM OF CETRORELIX ACETATE

FIELD OF THE INVENTION

The present invention relates to a stable parenteral dosage form with a ready-to-inject sterile stable aqueous solution of Cetrorelix acetate. The invention also relates to an injection device prefilled with the ready-to-inject sterile stable aqueous solution of Cetrorelix acetate. The present invention relates to a method of inhibiting premature luteinizing hormone surges in women undergoing controlled ovarian stimulation comprising a stable parenteral dosage form with a ready-to-inject sterile stable aqueous solution of Cetrorelix acetate.

BACKGROUND OF THE INVENTION

Cetrorelix is gonadotropin releasing hormone antagonist (GnRH antagonist) acetyl-D-3-(2'-naphtyl)-alanine-D-4-chlorophenylalanine-D-3-(3'-pyridyl)-alanine-L-serine-L-tyrosine-D-citruline-L-leucine-L-arginine-L-proline-D-alanine-amide ($C_{70}H_{92}ClN_{17}O_{14}$) having the following formula. It is a decapeptide with a terminal acid amide group. It acts by blocking the action of GnRH upon the pituitary, thus rapidly suppressing the production and action of leutinizing hormone and follicle stimulating hormone.

To Cetrorelix acetate solutions (2.5 mg/ml), gluconic acid was added, whereby at concentrations of gluconic acid less than 0.07%, resulting in a pH of 3.7, aggregation was seen within 2 days. Similar failure was reported when the pH was more than 3.7. When the concentration of gluconic acid was increased to 0.71%, resulting in a pH of 3.1, the aggregation was seen in 12 days indicating that higher concentrations of gluconic acid and thus lower pH led to improvement. The disadvantage of the method is that the degree of resolution of the problem of aggregation is dependent on the gluconic acid concentration and with more gluconic acid the pH decreases. However, U.S. Pat. No. 7,718,599 did not report the effect of pH on the chemical stability of Cetrorelix. Moreover, there were no formulations where aggregation was not seen during long term storage stability studies.

US 2013/0303464 discloses a ready-to-use aqueous preparation of Cetrorelix comprising Cetrorelix acetate, glacial acetic acid, a tonicity adjusting agent and water for injection. A suitable pH was illustrated by working examples where the pH was about 3. The preferred pH according to the invention was pH 2.8 to 3.5.

U.S. Pat. No. 7,214,662 disclosed aqueous solutions of peptides including Cetrorelix acetate and suggested solutions to the problem of aggregation. It taught that carboxylic acids and especially hydroxycarboxylic acids, preferably gluconic acid in combination with a surfactant reduces

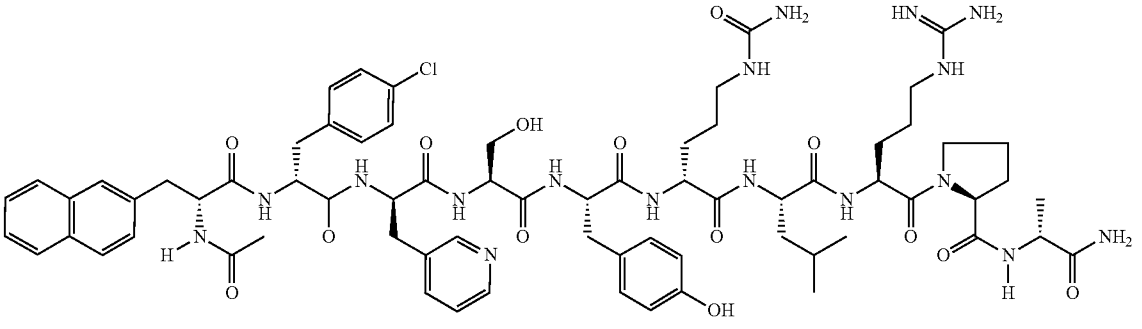

Aqueous solutions of peptides are required for parenteral administration. However, aqueous solutions of peptides such as Cetrorelix are susceptible to chemical degradation. They are also prone to aggregation whereby the turbidity or cloudiness of the solution increases on storage.

The first product on the market was Cetrotide®. It is available as a lyophilized powder in glass vials containing 0.25 mg or 3 mg of Cetrorelix. A prefilled glass syringe having 1 ml or 3 ml of sterile water for injection is provided separately and the solution is prepared only prior to injection. Therefore the first product solved the problem of degradation in aqueous solution simply by avoiding preparing a dosage form containing an aqueous solution that needed to be stored over time. Instead the water was removed and a lyophilizate was prepared to avoid instability problems. However, this solution to the problem has clear disadvantages—(1) expensive and time consuming process; (2) product is not ready-to-inject and requires reconstitution before administration; and (3) reconstituted solution is stable only for a short period of time. Cetrotide® thus did not fulfil a need for a ready-in inject aqueous solution.

U.S. Pat. No. 7,718,599 disclosed that aqueous solutions of Cetrorelix were prone to aggregation. Under polarized light microscope liquid crystalline structures were observed.

aggregation. The use of carboxylic acid according to U.S. Pat. No. 7,214,662 resulted in a low pH such as pH 2.5 to 3.

DESCRIPTION OF THE INVENTION

The object of the present invention is to provide a parenteral dosage form comprising a ready-to-inject sterile stable aqueous solution of Cetrorelix acetate. Another object of the invention is to provide an injection device pre-filled with the sterile stable aqueous solution of Cetrorelix acetate. The term "ready-to-inject" as used herein refers to a ready-to-inject, sterile stable aqueous solution of Cetrorelix acetate which is suitable for direct subcutaneous or intramuscular administration, i.e. it is ready-to-inject and there is no requirement of reconstitution or dilution before injection. More particularly, it is the object that the sterile stable aqueous solution of Cetrorelix acetate dispensed in an injection device be ready-to-inject, not only be physically stable in terms of control on aggregation or turbidity development but also be chemically stable such that impurities remain low while the parenteral dosage form is stored on the shelf and until it is injected into the patient subcutaneously or intra-muscularly.

Degradation of peptides can lead to generation of other peptides and/or peptide derivatives which may themselves have pharmacological activity. Therefore the objective more particularly was to develop an appropriate method to separate individual impurities and quantify them. The objective was to limit the concentration of such impurities. The inventors discovered a High Performance Liquid Chromatographic method which gave separate peaks for several impurities which were here before not reported in the prior art. Whereas the prior art advocated low pH values to decrease the tendency for agglomeration, the inventors found with the use of their HPLC method that in the parenteral dosage form of the present invention, a pH of 3 to 5 was optimal for chemical stability in terms of increases in level of impurities over a period of time and also the aqueous solution of Cetrorelix acetate could be prepared at this higher pH without agglomeration problems.

An impurity discovered by the inventors was Impurity A represented by the compound of Formula I given below.

Formula I

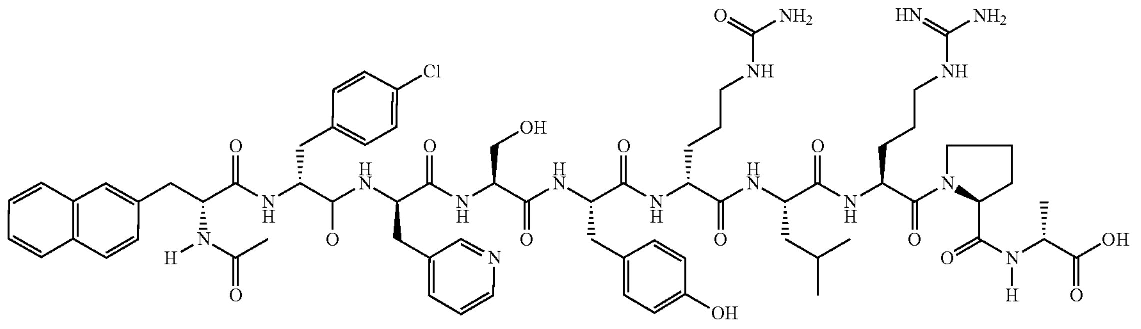

Impurity B is characterized to have a structure represented by the compound of Formula II given below:

Formula II

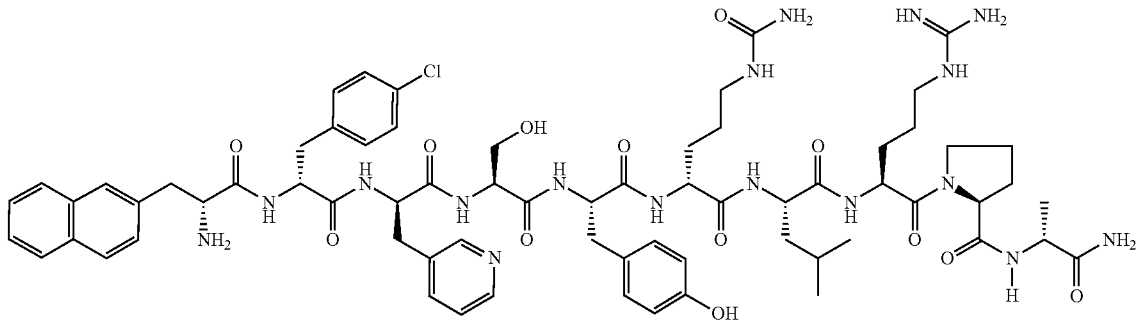

Impurity D is characterized to have a structure represented by the compound of Formula III given below:

Formula III

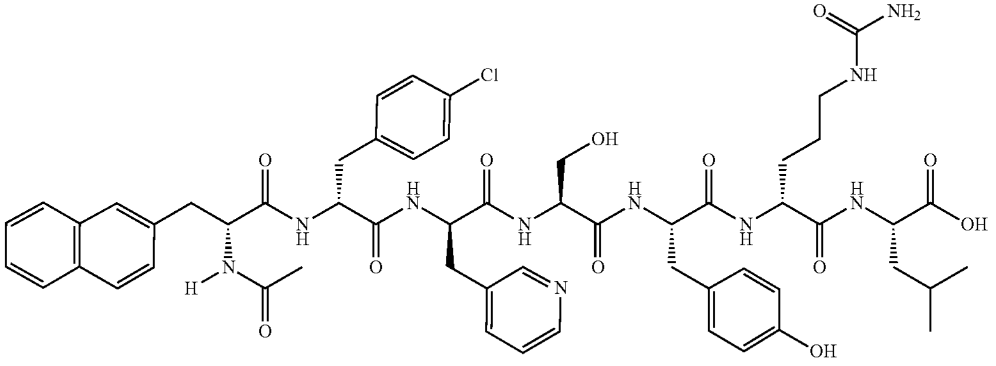

Impurity F is characterized to have a structure represented by the compound of Formula IV given below:

Formula IV

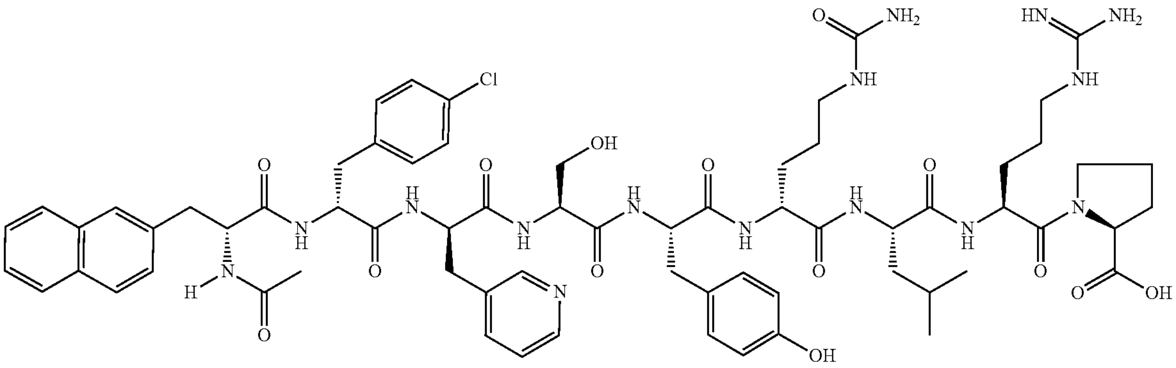

The prior art considered low pH of 3.0 to be the optimum pH for stability, however, the inventors found that at pH values of 2.5 to 3.0 advocated by the prior art, the level of Impurity A increases significantly upon storage of the solution at 25 °C/60% relative humidity. None of the prior art identified the compounds of formula I, II, III and IV, i.e. Impurities A, B, D and F respectively.

The present inventors found that not only the stable aqueous solution of Cetrorelix acetate could be prepared at a pH 3 to 5 without agglomeration problems but also the level of Impurity A and total impurities were well controlled and they remain at low concentrations upon storage of the parenteral dosage form at 25 °C/60% RH for at least 1 month, at least 2 months, at least 3 months, or at least 6 months. The parenteral dosage form could also be stored at 2 to 8 °C with good stability for at least 24 months.

In one aspect, the present invention provides a parenteral dosage form comprising a ready-to-inject sterile, stable aqueous solution comprising:

(i) Cetrorelix or a pharmaceutically acceptable salt thereof, (ii) an organic acid to adjust the pH in the range of 3 to 5, (iii) Impurity A, a decapeptide of formula I in an amount less than 1% w/v of Cetrorelix base Formula I

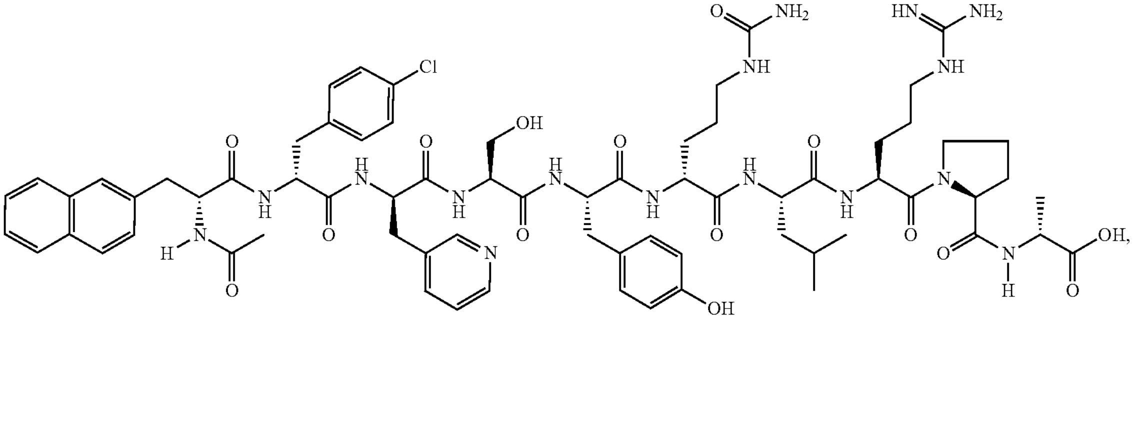

(iv) an osmotic agent; and (v) water for injection.

In one embodiment, the invention provides a parenteral dosage form comprising a ready-to-inject sterile, stable aqueous solution consisting of:

(i) Cetrorelix or a pharmaceutically acceptable salt thereof, (ii) an organic acid to adjust the pH in the range of 3 to 5, (iii) Impurity A, a decapeptide of formula I in an amount less than 1% w/v of Cetrorelix base Formula I

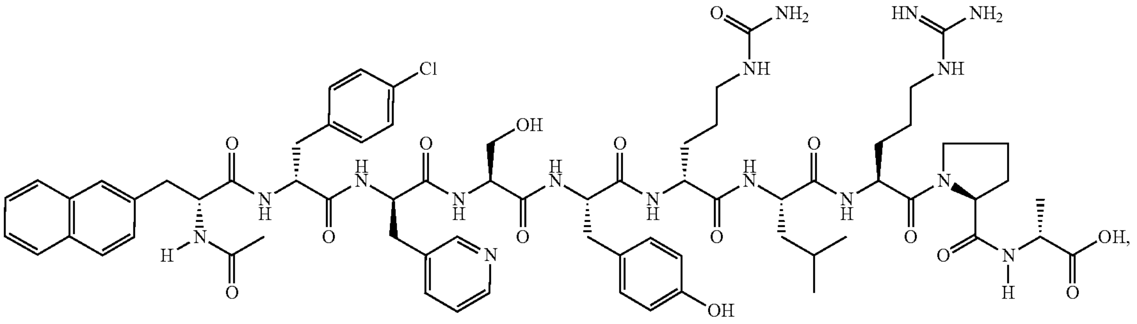

(iv) an osmotic agent, and (v) water for injection.

The parenteral dosage form comprising the ready-to-inject sterile, stable aqueous solution of Cetrorelix according to the present invention remains physically and chemically stable when stored at 2 to 8 °C for at least 1 month, at least 3 months, at least 6 months, at least 12 months, at least 18 months, or at least 24 months; or at room temperature (25 °C/60% RH) for at least 1 month, at least 3 months, or at least 6 months.

Preferred embodiments of the stable parenteral dosage form can be labelled with a shelf life at 2 to 8 °C of at least 24 months or of 24 months. More preferred embodiments of the parenteral dosage form can be labelled with a shelf life of at least 6 months or of 6 months at room temperature (25 °C/60% RH) storage condition.

The concentration of decapeptides of formula I (Impurity A) remains in the range of 0.001% to 1.0%, preferably 0.05 to 0.5% by weight of Cetrorelix base, single maximum unknown impurity remains less than 0.5% by weight of Cetrorelix base and total impurity remains not more than 3.5% by weight of Cetrorelix base upon storage at 2 to 8 °C for at least 1 month, at least 2 months, at least 3 months, at least 6 months, at least 12 months, at least 18 months or at least 24 months and/or at room temperature (25 °C/60% RH) for at least 1 month, at least 2 months, at least 3 months, or at least 6 months.

The parenteral dosage form comprising the ready-to-inject sterile aqueous solution of Cetrorelix according to the present invention is physically stable with no aggregation, gel formation or precipitation of the aqueous solution during the shelf-life. The aggregation or gel formation can be determined by measuring the cloudiness or turbidity of the solution. It is measured in FTU unit (Formazin Turbidity Unit) or NTU unit (Nephelometric Turbidity Unit). The test is performed according to the protocol described in European Pharmacopoeia 9.0. The solution is said to be free of any aggregation or gel formation if the cloudiness/turbidity value is less than or equal to 8 FTU/NTU. The higher the FTU/NTU values the higher the cloudiness or turbidity in the solution and vice-versa. The NTU values of the ready-to-inject parenteral dosage form according to the present invention remains less than 2 NTU, preferably less than 1 NTU, more preferably less than 0.5 NTU, initially and upon long term storage of the dosage form at 2 to 8 °C for at least 1 month, at least 2 months, at least 3 months, at least 6 months, at least 12 months, at least 18 months or at least 24 months and/or at room temperature (25 °C/60% RH) for at least 6 months. Thus, there occurs no aggregation, gel formation or precipitation of the aqueous solution during the shelf-life. Also, there occurs no substantial increase in viscosity of the solution upon storage.

The parenteral dosage form comprising the ready-to-inject sterile, stable aqueous solution of Cetrorelix according to the present invention contains Cetrorelix acetate at a concentration ranging from 0.26 mg/ml to 0.28 mg/ml, which amount is equivalent to 0.25 mg/ml of Cetrorelix base. Preferably, Cetrorelix acetate is present in the ready-to-inject sterile, stable aqueous solution at a concentration equivalent to 0.25 mg/ml of Cetrorelix base.

In one embodiment, the parenteral dosage form comprising the ready-to-inject sterile, stable aqueous solution of Cetrorelix according to the present invention comprises a pH adjusting agent at a concentration sufficient to adjust the pH in the range of 3 to 6.

In a preferred embodiment, the parenteral dosage form comprising the ready-to-inject sterile, stable aqueous solution of Cetrorelix according to the present invention comprises an organic acid as a pH adjusting agent at a concentration sufficient to adjust the pH in the range of 3 to 5, more preferably in the range of 4 to 4.5. The pH of the ready-to-inject sterile, stable aqueous solution according to the present invention may be for example, 3, 3.05, 3.10, 3.15, 3.20, 3.25, 3.30, 3.35, 3.40, 3.45, 3.5, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55 and 6 or intermediate ranges thereof.

The organic acid may be selected from any parenterally acceptable organic acid soluble in water but is preferably acetic acid, more preferably lactic acid. For example, lactic acid may be used in the ready-to-inject sterile aqueous solution according to the present invention at a concentration ranging from about 0.013 mg/ml to 0.53 mg/ml, preferably in amount ranging from about 0.033 mg/ml to about 0.53 mg/ml; and intermediate ranges thereof.

Preferably, according to the present invention, the ready-to-inject sterile, stable aqueous solution of Cetrorelix comprise Cetrorelix (base) and organic acid in a weight ratio ranging from 0.47:1 to 19.23:1, preferably in a weight ratio ranging from about 0.47:1 to 7.57:1, more preferably in a weight ratio ranging from about 1.56:1 to 7.57:1 and intermediate ranges thereof.

The parenteral dosage form comprising the ready-to-inject sterile, stable aqueous solution of Cetrorelix according to the present invention comprises an osmotic agent or tonicity adjusting agent, in amounts suitable to adjust the osmolality of the solution in the range of about 250-375 mOsm/kg, preferably 270-330 mOsm/kg. The osmotic agent that may be used in the aqueous solution according to present invention is selected from, but not limited to, mannitol, glycerol, sorbitol, sodium chloride, potassium chloride, dextrose, sucrose, and the like and mixtures thereof. According to one preferred embodiment, the osmotic agent is mannitol and it may be used in the aqueous solution in an amount ranging from about 40.0 mg/ml to 60.0 mg/ml, preferably in an amount ranging from about 50.0 mg/ml to 58.0 mg/ml. In one preferred embodiment, the osmotic agent is mannitol and it is used in the ready-to-inject sterile aqueous solution in an amount of about 55.0 mg/ml.

The ready-to-inject sterile, aqueous solution of the parenteral dosage form of the present invention does not contain lactic acid in the form of its derivatives, polymer or copolymers such as polylactic acid or polylactic-co-glycolic acid. Preferably, lactic acid is used as a sole pH adjusting agent. In preferred embodiments, the ready-to-inject sterile, aqueous solution is free of any surfactant, such as tween 80, polysorbates, poloxamers, spans and the like. The ready-to-inject sterile, aqueous solution of the parenteral dosage form avoids use of surfactants, complexing agents, preservative or anti-oxidants for solubilization or stabilization. In certain embodiments, the solution is free of complexing agents like cyclodextrins, free of co-solvents such as alcohols or glycols and is also free of preservatives and antioxidants.

In another aspect, the present invention provides the sterile aqueous solution of Cetrorelix acetate as above which remains stable for at least 1 month, preferably for at least 3 months and more preferably for at least 6 months at 25 °C temperature and 60% relative humidity.

In yet another aspect, the present invention provides the sterile aqueous solution of Cetrorelix acetate as above which remains stable for at least 1 month, preferably for at least 3 months, more preferably for at least 6 months, even more preferably for at least 12 months or 18 months, and most preferably for at least 24 months at 2-8 °C The stable parenteral dosage form comprising the ready-to-inject sterile, stable aqueous solution of Cetrorelix according to the present invention is suitable for administration by subcutaneous route or intra-muscular route. The ready-to-inject sterile, stable aqueous solution is suitable for direct subcutaneous administration, i.e. it is ready-to-inject or ready-to-self-administer and there is no requirement of reconstitution or dilution before use. The ready-to-inject sterile, stable aqueous solution according to the present invention does not involve lyophilization.

The stable parenteral dosage form of the present invention is suitable for self-administration and enables the patient to self-administer a small volume of the aqueous solution subcutaneously. The volume of the ready-to-inject sterile, aqueous solution of Cetrorelix filled in the reservoir of the injection device ranges from about 0.5 ml to 10.0 ml, preferably 1.0 ml to 2.0 ml, more preferably 1.0 ml. According to one of the preferred embodiments, the ready-to-inject sterile, stable aqueous solution of Cetrorelix is filled in the reservoir of the injection device in volume of 1.0 ml. Preferably the parenteral dosage form according to the present invention is suitable for administering a single dose of Cetrorelix acetate. In one embodiment, the parenteral dosage form comprises a fill volume of about 1.0 ml of aqueous solution of Cetrorelix acetate suitable for self-administration as a single dose. In some embodiment, the parenteral dosage form may comprise aqueous solution of Cetrorelix at a fill volume of about 10.0 ml, suitable for multiple dose administration.

The injection device according to the stable parenteral dosage form of the present invention may be selected from, but not limited to, prefilled syringes, autoinjectors and the like. In one preferred embodiment, the injection device is a prefilled syringe. In another preferred embodiment, the injection device is an autoinjector such as a pen autoinjector. These pre-filled syringes or auto-injectors are suitable for self-administration or auto-injection of the drug solution by the patients in need thereof, thus providing a user friendly approach.

In one preferred embodiment, the injection device is a prefilled syringe. The prefilled syringe comprises following components: a reservoir such as, for example, a barrel or a cartridge which stores the aqueous solution; a stalked needle attached at one end of the reservoir; a needle shield or tip cap that covers the needle and seals the needle tip opening, optionally, a rigid shield covering the needle shield or tip cap; a plunger stopper at other end of the reservoir that stoppers and seals the aqueous solution filled in the reservoir; a plunger rod that fits into the plunger stopper and is used to push the plunger stopper along with the solution towards the needle end while administering the drug.

In another preferred embodiment, the injection device is an autoinjector. The auto-injector can have varied designs. In one preferred design, the autoinjector comprises the following components: a central assembly or body portion that is suitable to hold a pre-filled syringe, the syringe comprising a reservoir such as a barrel or a cartridge which stores the aqueous solution, the reservoir having a stalked needle at one end and a plunger stopper at other end. The central body portion may have a clear inspection window through which the solution in reservoir is visible. The autoinjector further comprises a front assembly having a cap portion that holds a needle shield or tip cap, and it is attachable to the central assembly covering the stalked needle and sealing the needle tip opening. The autoinjector further comprises a rear assembly which comprises a plastic rod with a spring assembly and an activation button. During self-administration of the aqueous solution, first, the cap along with needle shield is removed from the body portion exposing the needle and subsequently after placing the body portion of the autoinjector at the site of administration the activation button is pressed, which pushes the plastic rod with spring assembly towards the plunger stopper which leads to delivery of the aqueous solution through the needle to the patient.

The reservoir may be a barrel or a cartridge, such as, for example, a barrel of a pre-filled syringe or a cartridge of an auto-injector. It may be made up of a material selected from glass, plastic or a polymeric material. In some preferred embodiments, the reservoir is made up of glass, such as USP Type I siliconized glass or non-pyogenic glass material. In other embodiments, the reservoir is made up of a non-glass plastic or polymeric material selected from cycloolefin polymer, cycloolefin copolymer, polyolefins, styrene-polyolefin based polymers and block co-polymers, polycarbonates and the like. In one preferred embodiment, the reservoir is a non-pyogenic glass barrel of a pre-filled syringe or non-pyogenic glass cartridge of an auto-injector.

In one or more embodiments, the reservoir may have a stacked needle at one end. In some other embodiments, the reservoir is needleless and has a luer tipped lock at one end with provision for attaching a needle at the leur tip before use. The stalked needle may be made up of stainless steel. The needle tip is shielded or covered with a needle shield or tip cap. The reservoir containing the sterile aqueous solution of drug is further sealed with a stopper such as a plunger stopper at the other end. These stoppers, needle shields or tip caps provide a physical and sterility barrier against exterior environment.

Preferably, the plunger stopper, the needle shield/tip cap or the cap of leur lock is made up of a non-glass component. The non-glass component may be a rubber or elastomeric material such as for example, bromobutyl rubber, chlorobutyl rubber, USP type II rubber, natural rubber made up of poly-cis-1,4-isoprene, styrene butadiene rubber and the like. Other suitable materials include high density polyethylene or low density polyethylene or other plastic materials. In preferred embodiments, the plunger stopper is made up of bromobutyl rubber and the needle shield or tip cap is made up of natural rubber. The needle shield may further be covered on an outer side by a rigid shield made up of polypropylene. It protects the needle shield from damage and enhances removal of needle shield before injection. The injection device assembly may have a plunger rod that attaches to the plunger stopper and is used to push the plunger stopper along with the solution towards the needle end while administering the drug.

Preferably, the ready-to-inject sterile, stable aqueous solution of Cetrorelix is filled in the reservoir of the injection device and stoppered in such a manner that there is substantially no headspace air left inside the reservoir. The aqueous solution in the reservoir always remains in contact with the plunger stopper made up of elastomeric or rubber material during storage. In the case of prefilled syringes having a stalked needle made up of stainless steel, the needle being covered by a needle shield or tip cap, the aqueous solution remains in contact with the needle and the needle shield or tip cap during storage.

The injection device may optionally be packaged or enclosed in a secondary packaging. The secondary packaging may be a blister pack or an aluminum pouch and/or an opaque carton. A suitable oxygen scavenger may optionally be placed inside the secondary packaging.

The stability testing of the parenteral dosage form is done by storing the dosage form at 2-8 °C and at room temperature (25 °C/60% relative humidity). During stability testing, the ready-to-inject sterile solution of Cetrorelix remains in contact with the plunger stopper and needle shield made up of elastomeric rubber material as well as with the stacked needle made up of stainless steel.

In preferred embodiments, the parenteral dosage form comprising the ready-to-inject sterile aqueous solution of Cetrorelix according to the present invention remains physically and chemically stable for a period of 1 year, preferably 2 years when stored at 2-8 °C and at least for 6 months at room temperature (25 °C, 60% relative humidity). The concentration of Impurity A remains less than 1.0% by weight of Cetrorelix base upon storage of the filled injection device at room temperature (25 °C/60% relative humidity) for at least 6 months and at 2-8 °C for at least 24 months. The extrapolated shelf life of the aqueous solution of Cetrorelix determined by Minitab computation for Impurity A considering levels of not more than 1%, is found to be 122 months.

In one aspect, the present invention relates to a method of inhibiting premature luteinizing hormone surges in women undergoing controlled ovarian stimulation comprising: a parenteral dosage form comprising: a ready-to-inject sterile, stable aqueous solution comprising:

(i) Cetrorelix or a pharmaceutically acceptable salt thereof,
(ii) an organic acid to adjust the pH in the range of 3 to 5,
(iii) Impurity A, a decapeptide of formula I in an amount less than 1% w/v of Cetrorelix base, Formula I

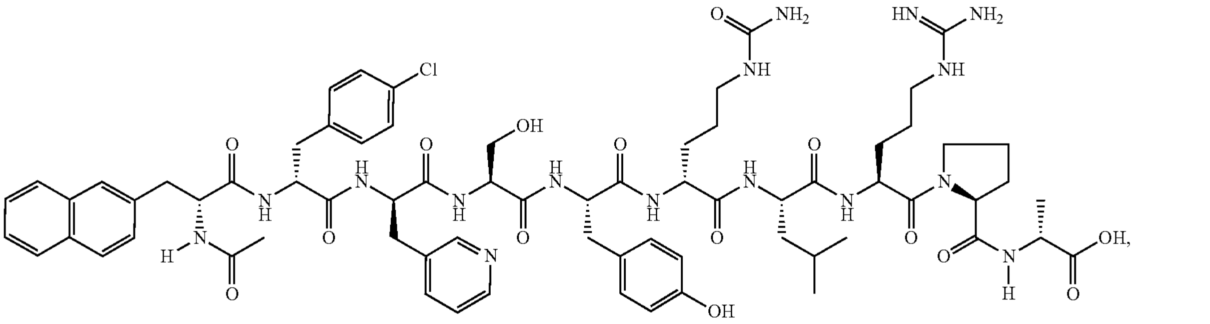

(iv) an osmotic agent, and (v) water for injection.

Hereinafter, the invention will be more specifically described by way of Examples. The examples are not intended to limit the scope of the invention and are merely used as illustrations.

EXAMPLE 1A

Identification of the Degradation Product

In order to investigate the degradation of Cetrorelix, peptide related substances of Cetrorelix were prepared by the known technique of solid phase peptide synthesis. The synthesis involved coupling of one amino acid at a time sequentially starting from c-terminal amino acid on a resin. The synthesis of the peptide chain was carried out using the Fluorenylmethyloxycarboyl (Fmoc)/tButyl (Fmoc/tBu) with N,N'-diisopropyl carbodiimide (DIPC) as the coupling reagent. The Fmoc groups were removed via treatment with 20% piperidine in dimethylformamide. The peptide formed on resin was finally cleaved using trifluoroacetic acid to obtain related substances which were further purified by reverse phase high performance liquid chromatography (RP-HPLC) on a C18 Silica column using a gradient of acetonitrile/water containing 0.1% trifluoroacetic acid. The purified peptide related substances were lyophilized to obtain pure solid form. The structure of these related substances were characterized by Proton NMR, Carbon NMR, Mass spectroscopy and elemental analysis and they were referred to as Impurity A, B, D and F.

Impurity-A:—Ac-2-D-Nal-4-Cl-D-Phe-3-D-Pal-Ser-Tyr-D-Cit-Leu-Arg-Pro-D-Ala-OH (detailed structure depicted as the Compound of Formula I), Impurity-B:—2-D-Nal-4-Cl-D-Phe-3-D-Pal-Ser-Tyr-D-Cit-leu-Arg-Pro-D-Ala-$NH_2$ (detailed structure depicted as the Compound of Formula II), Impurity-D:—Ac-2-D-Nal-4-Cl-D-Phe-3-D-Pal-Ser-Tyr-D-Cit-Leu-OH (detailed structure depicted as the Compound of Formula III), Impurity-F:—Ac-2-D-Nal-4-Cl-D-Phe-3-D-Pal-Ser-Tyr-D-Cit-Leu-Arg-Pro-OH (detailed structure depicted as the Compound of Formula IV).

The degradation peaks separated on the HPLC column, were identified to be these compounds based on their relative retention time. The details of the HPLC method is provided in Example 1B below:

EXAMPLE 1B

Cetrorelix and the identified impurities namely, Impurity A, Impurity B, Impurity D and Impurity F from the aqueous solution samples were separated on a reverse phase (C-18) column using gradient technique (Column: X-Select CHS C18, (150×4.6) mm, 2.5μ (by Waters, Ireland, Part No: 186006729), detected and quantified by Ultraviolet spectroscopy at 225 nm wavelength. The mobile phase was run at a flow rate of 0.7 ml/min and 1.0 ml/min. The run time of the chromatogram was 150 minutes.

Mobile Phase Details:

Mobile Phase A: A mixture of buffer solution as below, with acetonitrile and tetrahydrofuran in the ratio of (700:280:20), degassed by sonication.

Mobile Phase B: A mixture of buffer solution as below, with acetonitrile and tetrahydrofuran in the ratio of (500:480:20), degassed by sonication.

Buffer: 2.5 g of Ammonium dihydrogen orthophsphate and 0.75 g of 1-Octane sulphonic acid sodium salt in 1000 ml water with pH adjusted to 8.0±0.05 using triethylamine.

Diluent: A mixture of water, acetonitrile and formic acid in the ratio of (700:300:1).

TABLE 1

| Details of gradient elution | | | |
|---|---|---|---|
| Time (minutes) | Flow Rate | Mobile Phase A (% v/v) | Mobile Phase B (% v/v) |
| 0 | 0.7 | 100 | 0 |
| 65 | 0.7 | 100 | 0 |
| 75 | 0.7 | 0 | 100 |
| 76 | 1.0 | 0 | 100 |
| 135 | 1.0 | 0 | 100 |
| 136 | 0.7 | 100 | 0 |
| 150 | 0.7 | 100 | 0 |

Preparation of the Stock Solution of Impurities:

3.125 mg each of Impurity A; Impurity B, Impurity D and Impurity F were taken in a 50 ml volumetric flask and dissolved in about 5 ml of diluent by sonication, followed by making up the volume using the diluent.

Preparation of System Suitability Solution:

This was prepared by weighing and transferring about 12.5 mg of Cetrorelix acetate working standard in 100 ml volumetric flask and dissolving it in about 50 ml of diluent by sonication, followed by addition of about 2 ml of impurity stock solution and making up the volume using the diluent.

Preparation of the Standard Solution of Cetrorelix Acetate:

The standard solution of Cetrorelix acetate was prepared by weighing and transferring 20 mg of Cetrorelix acetate working standard into 250 ml volumetric flask and dissolving it in about 50 ml of diluent by sonication and making up the volume with the diluent. Two ml of this solution was transferred into 250 ml volumetric flask and volume made up to the mark using the diluent with mixing.

Preparation of Test Solution:

The aqueous solution of Cetrorelix acetate from about 10 pre-filled syringes of the sample to be tested (prepared according to example as described above) was mixed in a container. The solution comprises Cetrorelix acetate, an organic acid, an osmotic agent and water for injection. Accurately about 5.0 ml of this solution was transferred in 10 ml volumetric flask and about 3 ml of the diluent was added and the solution was sonicated for 5 minutes with intermediate shaking. Volume made up using the diluent with mixing.

The placebo was prepared by transferring accurately about 5.0 ml of placebo solution in 10 ml volumetric flask, adding about 3 ml diluent and sonicating for 5 minutes with intermediate shaking. Volume made up using the diluent with mixing.

50 microlitres injections in duplicate of diluent as blank were injected into the chromatographic system. Subsequently, the system suitability solution was injected and the chromatogram was recorded. The resolution between Cetrorelix acetate Impurity D and Cetrorelix acetate Impurity F is not less than 2.0. Following this, six replicates of standard solution were injected. Subsequently, the sample and placebo preparation was injected into the chromatographic system.

The relative retention time and relative response factor of Cetrorelix acetate and Impurities A, B, D and F with respect to Cetrorelix acetate are presented in table 2 below.

TABLE 2

| Name of compound | Retention Time (minute) | Relative retention time |
|---|---|---|
| Cetrorelix | 42.3 | 1.00 |
| Impurity A | 23.5 | 0.55 |
| Impurity B | 56.8 | 1.34 |
| Impurity D | 16.9 | 0.39 |
| Impurity F | 20.3 | 0.48 |

The percentage of Impurities A, B, D, F and unknown impurity was calculated excluding peaks from diluent and placebo. The sum of all known and unknown impurities provided % total impurities.

The % of identified impurities (A, B, D, F) was calculated by following formula:

$$\frac{A1}{AS}\times\frac{WS}{250}\times\frac{2}{250}\times\frac{10}{V}\times\frac{P}{LC}\times\frac{1}{RRF}$$

Where,

A1=Peak response of each known impurity in the chromatogram of test preparation

AS=Average peak response of Cetrorelix in the chromatogram of standard preparation WS=Weight of Cetrorelix acetate working standard in mg V=Volume of sample taken in ml P=% potency of Cetrorelix working standard (on as is basis)

LC=Label claim of Cetrorelix in mg per ml (0.25 mg/ml)

RRF=Relative response factor of each Impurity

The % of Unknown impurity was calculated by following formula $$\frac{A1}{AS}\times\frac{WS}{250}\times\frac{2}{250}\times\frac{10}{V}\times\frac{P}{LC}$$

Where,

A1=Peak response of each unknown impurity in the chromatogram of test preparation AS=Average peak response of Cetrorelix in the chromatogram of Standard preparation WS=Weight of Cetrorelix acetate working standard in mg V=Volume of sample taken in ml P=% potency of Cetrorelix working standard (on as is basis)

LC=Label claim of Cetrorelix in mg per ml (0.25 mg/ml)

The total impurities (%)=Sum of % known impurities and % unknown impurities.

TABLE 3

| Composition | | | | | | | | | | | | | | |
|---|---|---|---|---|---|---|---|---|---|---|---|---|---|---|
| | Examples of the invention | | | | | | | | | Comparative examples | | | | |
| | Example Numbers | | | | | | | | | | | | | |
| | 1 | 2 | 3 | 4 | 5 | 6 | 7 | 8 | 9 | 10 | 11 | 12 | 13 | 14 |
| Ingredients | Quantity (mg/ml) | | | | | | | | | | | | | |
| Cetrorelix acetate expressed as Cetrorelix base | 0.25 | 0.25 | 0.25 | 0.25 | 0.25 | 0.25 | 0.25 | 0.25 | 0.25 | 0.25 | 0.25 | 0.25 | 0.25 | 0.25 |
| Mannitol | 54.8 | 54.8 | 54.8 | 54.8 | 54.8 | 54.8 | 54.8 | 54.8 | 54.8 | 54.8 | 54.8 | 54.8 | 54.8 | 54.8 |
| Lactic acid | q.s to adjust pH | | | | | | | | | | | | | |
| pH | 3 | 3.1 | 3.2 | 3.3 | 3.4 | 3.5 | 4 | 4.5 | 5 | 2.5 | 2.6 | 2.7 | 2.8 | 2.9 |
| Water for injection | q.s to 1 ml | | | | | | | | | | | | | |

Method of Preparation:

Water for injection was taken at temperature between 2 °C to 8 °C in a vessel. Mannitol was added and dissolved gradually in water for injection with stirring, until a clear solution was obtained. To this Cetrorelix acetate was added and dissolved gradually with stirring. The pH of the solution was checked and was adjusted to the pH as mentioned in Table 3 for each example of the invention and comparative examples, using specified amount (volume) of 0.1% w/v lactic acid solution. The volume was made up with water for injection. The solutions were stirred for 10-15 minutes. The solutions of the Examples were filtered aseptically through a bed of 0.2 micron membrane filter. The solution was aseptically filled in the reservoir of injection device, i.e. in the barrel of 1 ml glass syringe with a fill volume of 1.1 ml. The stacked needle in the barrel was stoppered by elastomeric needle shield, covered by a rigid cap before filling. After filling, the glass syringe (barrel) was stoppered with plunger stopper by vacuum stoppering in such a manner that there was substantially no headspace air left inside the syringe. The aqueous solution remains in contact with the plunger stopper made up of rubber, stacked needle made up of stainless steel and needle shield made up of natural rubber upon storage.

The ready-to-inject aqueous solution of working examples 1 to 9 and comparative examples 10 to 14 were subjected to chemical analysis at different stages. Initially, the % assay of Cetrorelix in the solution before and after filtration was analyzed by the HPLC method described above. The change in the chemical assay % before and after filtration was determined. The solutions of the examples contained in the glass syringes were then subjected to storage stability testing. The % assay, the level of degradation products like the compounds of formula I, II, III and IV and the level of unknown and total impurities in the filtered solution filled in injection device of the parenteral dosage form at initial time point and upon storage at different time points at room temperature (25 °C/60% relative humidity) and at 2 to 8 °C were determined using the high performance liquid chromatographic method described above.

It was found that after 3 months of storage at room temperature the level of Impurities A, B, single maximum unknown impurity and the total impurities remained unchanged or the change was small. Based on this data it is expected that the parenteral dosage form of the present invention is chemically stable over a long period of time. It was found that the solutions did not exhibit any problems of agglomeration or increase in viscosity when prepared and when filled into the injection device and stored. The data also demonstrated that there was no absorption or adsorption of Cetrorelix onto or into the components of the device, for instance, the rubber stopper which was in contact with the solution during the period of storage.

The stability results for the stable parenteral dosage form at 25 °C/60% RH and 2-8 °C according to the present invention are provided in Table 4 and Table 5 below:

TABLE 4

| | Observation at different time points upon storage at (25° C./60% RH) | | | | | | | | | | | | | | | |
|---|---|---|---|---|---|---|---|---|---|---|---|---|---|---|---|---|
| pH | Impurity A (%) | | | | Impurity B (%) | | | | Single maximum unknown impurity (%) | | | | Total impurity (%) | | | |
| | Time points (months) | | | | | | | | | | | | | | | |
| | 0 | 1 | 3 | 6 | 0 | 1 | 3 | 6 | 0 | 1 | 3 | 6 | 0 | 1 | 3 | 6 |
| 3 | BQL | 0.20 | 0.54 | 1.0 | 0.055 | ND | ND | BQL | 0.113 | 0.123 | 0.112 | 0.431 | 0.363 | 0.398 | 0.748 | 1.829 |
| 3.5 | BQL | 0.07 | 0.23 | 0.40 | 0.068 | ND | BQL | BQL | 0.105 | 0.148 | 0.189 | 0.392 | 0.335 | 0.292 | 0.623 | 1.059 |
| 4 | BQL | BQL | 0.09 | 0.15 | 0.039 | ND | ND | ND | 0.095 | 0.162 | 0.196 | 0.388 | 0.308 | 0.302 | 0.496 | 0.792 |
| 4.5 | ND | BQL | BQL | 0.04 | 0.058 | ND | ND | ND | BQL | 0.159 | 0.204 | 0.331 | 0.308 | 0.237 | 0.331 | 0.563 |
| 5 | BQL | BQL | — | — | ND | BQL | — | — | 0.119 | 0.125 | | | 0.205 | 0.208 | — | — |

ND: Not Detected;
RH—Relative Humidity;
BQL: Below Quantifiable limit

TABLE 5

| | Observation at different time points upon storage at (2-8° C.) | | | | | | | | | | | | | | | |
|---|---|---|---|---|---|---|---|---|---|---|---|---|---|---|---|---|
| pH | Impurity A (%) | | | | Impurity B (%) | | | | Single maximum unknown impurity (%) | | | | Total impurity (%) | | | |
| | Time points (months) | | | | | | | | | | | | | | | |
| | 0 | 1 | 3 | 6 | 0 | 1 | 3 | 6 | 0 | 1 | 3 | 6 | 0 | 1 | 3 | 6 |
| 3 | BQL | 0.05 | 0.08 | 0.18 | 0.055 | ND | ND | ND | 0.113 | 0.079 | 0.08 | 0.146 | 0.363 | 0.206 | 0.161 | 0.333 |
| 3.5 | BQL | BQL | BQL | 0.06 | 0.068 | BQL | ND | ND | 0.105 | 0.087 | 0.069 | 0.135 | 0.335 | 0.087 | 0.069 | 0.197 |
| 4 | BQL | BQL | BQL | 0.03 | 0.039 | ND | ND | ND | 0.095 | 0.16 | 0.144 | 0.138 | 0.308 | 0.23 | 0.144 | 0.174 |
| 4.5 | ND | BQL | ND | BQL | 0.058 | ND | ND | ND | BQL | 0.142 | 0.136 | 0.136 | 0.308 | 0.213 | 0.136 | 0.136 |

ND: Not Detected;
RH—Relative Humidity;
BQL: Below Quantifiable limit

TABLE 6

| | | | Assay of Cetrorelix acetate eq. to Cetrorelix (%) Storage conditions | | | | | | | |
|---|---|---|---|---|---|---|---|---|---|---|
| | | | 2-8° C. | | | | 25° C./60% RH | | | |
| pH | Unfiltered | Initial | 1 M | 2 M | 3 M | 6 M | 1 M | 2 M | 3 M | 6 M |
| 2.5 | 104.05 | 103.97 | 103.03 | 105.51 | 105.04 | 104.54 | 102.76 | 102.9 | 102.9 | 99.97 |
| 3 | 103.56 | 101.11 | 101.8 | 104.9 | 105.42 | 104 | 102.09 | 104.71 | 105.08 | 102.36 |
| 3.5 | 103.86 | 102.51 | 101.82 | 104.88 | 102.88 | 104.2 | 103.65 | 103.62 | 102.23 | 103.68 |
| 4 | 103.76 | 102.96 | 104 | 104.17 | 104.75 | 104.84 | 102.58 | 103.28 | 103.72 | 103.39 |
| 4.5 | 102.52 | 99.56 | 103.43 | 103.97 | 103.57 | 103.59 | 101.66 | 103.62 | 102.79 | 102.77 |
| 5 | 99.48 | — | — | — | — | — | 99.02 | — | — | — |

The stability results for additional intermediate pH ranges were studied at different time points upon storage at 25° C./60% RH and 2-8° C. are given in Table 7 below:

TABLE 7

| | | Observation at different time points upon storage | | | | | | | | | | | |
|---|---|---|---|---|---|---|---|---|---|---|---|---|---|
| | pH | Impurity A (%) | | | | | | Impurity B (%) | | | | | |
| | | Time points (months) | | | | | | | | | | | |
| Time | | 0 M | | | 1 M | | | 0 M | | | 1 M | | |
| points | | I | II | III | I | II | III | I | II | III | I | II | III |
| At | 3.1 | 0.04 | NA | NA | 0.28 | 0.27 | 0.27 | ND | NA | NA | ND | ND | — |
| (25° C. | 3.2 | BQL | NA | NA | 0.29 | 0.29 | 0.30 | ND | NA | NA | BQL | BQL | BQL |
| 60% RH) | 3.3 | BQL | NA | NA | 0.17 | 0.18 | 0.17 | ND | NA | NA | ND | ND | ND |
| | 3.4 | BQL | NA | NA | 0.2 | 0.2 | 0.20 | ND | NA | NA | ND | ND | ND |
| At | 3.1 | 0.04 | NA | NA | 0.14 | 0.15 | 0.14 | ND | NA | NA | ND | ND | ND |
| 2-8° C. | 3.2 | BQL | NA | NA | 0.14 | 0.15 | 0.15 | ND | NA | NA | ND | ND | ND |
| | 3.3 | BQL | NA | NA | 0.1 | 0.09 | 0.10 | ND | NA | NA | ND | ND | ND |
| | 3.4 | BQL | NA | NA | 0.09 | 0.10 | 0.09 | ND | NA | NA | ND | ND | ND |

| | | Observation at different time points upon storage | | | | | | | | | | | |
|---|---|---|---|---|---|---|---|---|---|---|---|---|---|
| | pH | Single maximum unknown impurity (%) | | | | | | Total impurity (%) | | | | | |
| | | Time points (months) | | | | | | | | | | | |
| Time | | 0 M | | | 1 M | | | 0 M | | | 1 M | | |
| points | | I | II | III | I | II | III | I | II | III | I | II | III |
| At | 3.1 | 0.13 | NA | NA | 0.15 | 0.124 | 0.143 | 0.178 | NA | NA | 0.567 | 0.517 | 0.55 |
| (25° C. | 3.2 | 0.129 | NA | NA | 0.136 | 0.141 | 0.138 | 0.129 | NA | NA | 0.569 | 0.57 | 0.571 |
| 60% RH) | 3.3 | 0.137 | NA | NA | 0.139 | 0.153 | 0.137 | 0.228 | NA | NA | 0.512 | 0.448 | 0.429 |
| | 3.4 | 0.131 | NA | NA | 0.165 | 0.15 | 0.12 | 0.201 | NA | NA | 0.523 | 0.49 | 0.485 |
| At | 3.1 | 0.13 | NA | NA | 0.128 | 0.115 | 0.123 | 0.178 | NA | NA | 0.381 | 0.361 | 0.365 |
| 2-8° C. | 3.2 | 0.129 | NA | NA | 0.134 | 0.127 | 0.127 | 0.129 | NA | NA | 0.423 | 0.436 | 0.48 |
| | 3.3 | 0.137 | NA | NA | 0.123 | 0.126 | 0.12 | 0.228 | NA | NA | 0.315 | 0.4 | 0.386 |
| | 3.4 | 0.131 | NA | NA | 0.123 | 0.128 | 0.124 | 0.201 | NA | NA | 0.333 | 0.332 | 0.327 |

ND: Not Detected;

RH—Relative Humidity;

BQL: Below Quantifiable limit;

NA: Not Available

TABLE 8

| | Assay of Cetrorelix acetate eq. to Cetrorelix (%) Storage conditions | | | |
|---|---|---|---|---|
| pH | Unfiltered | Initial | 2-8° C. 1 M | 25° C./60% RH 1 M |
| 3.1 | 99.96 | 98.67 | 99.12 | 98.65 |
| 3.2 | 100.89 | 100.21 | 99.9 | 100.06 |
| 3.3 | 99.96 | 99.05 | 98.58 | 98.97 |
| 3.4 | 100.02 | 98.54 | 99.59 | 99.91 |

Table 9
Stability Data of Cetrorelix Acetate Injection 0.25 mg/ml, 1 ml PFS at pH 5

Each mL contains Cetrorelix acetate eq. To Cetrorelix 0.25 Mg, Mannitol 54.8 mg, Lactic acid q.s. to pH adjusted 5.0, Water For Injection q.s. to 1 mL

TABLE 9

Stability data of Cetrorelix acetate Injection 0.25 mg/ml, 1 ml PFS at pH 5
Each mL contains Cetrorelix acetate eq. To Cetrorelix 0.25 Mg, Mannitol 54.8 mg, Lactic acid q.s. to pH adjusted 5.0, Water For Injection q.s. to 1 mL

| | | | Assay of | Related Substances | | | |
|---|---|---|---|---|---|---|---|
| | | | Cetrorelix acetate eq. To Cetrorelix | Known Impurities | | UnKnown Impurities Highest UnKnown | Total |
| | | Description | 95.0% to 105.0% of LC | Impurity A Not more than 1.0% | Impurity B Not more than 1.0% | Impurity Not more than 0.5% | Impurities Not more than 3.5% |
| UNFILTER | | * | 99.59 | | | | |
| INITIAL | | * | 99.67 | BQL (<0.035%) | ND | 0.131 | 0.131 |
| 2-8° C. OTS | 1M | * | 98.13 | BQL (<0.035%) | ND | 0.11 | 0.182 |
| | 2M | * | 98.6 | ND | ND | 0.109 | 0.208 |
| | 3M | * | 99.98 | ND | ND | 0.112 | 0.198 |
| 25° C./60% RH OTS | 1M | * | 98 | BQL (<0.035%) | ND | 0.106 | 0.106 |
| | 2M | * | 98.24 | 0.074 | ND | 0.109 | 0.369 |
| | 3M | * | 98.18 | 0.18 | ND | 0.107 | 0.353 |

ND: Not Detected;
RH—Relative Humidity;
BQL: Below Quantifiable limit;
* Clear colorless solution filled in 1 ml PFS

TABLE 10

| | | Observation at different time points upon storage | | | | | | | | | | | | |
|---|---|---|---|---|---|---|---|---|---|---|---|---|---|---|
| | pH | Impurity A (%) | | | | | | Impurity B (%) | | | | | | Single maximum unknown impurity (%) |
| | Time points (months) | | | | | | | | | | | | | |
| Time | | 0 M | | | 1 M | | | 0 M | | | 1 M | | | 0 M |
| points | | I | II | III | I | II | III | I | II | III | I | II | III | I |
| At | 2.5 | 0.08 | — | — | 0.82 | — | — | 0.072 | — | — | BQL | — | — | 0.105 |
| (25° C. | 2.6 | 0.08 | 0.08 | 0.08 | 1.28 | 1.29 | 1.29 | ND | — | — | ND | ND | ND | 0.138 |
| 60% RH) | 2.7 | 0.58 | 0.59 | 0.58 | 0.99 | 1.00 | 0.98 | ND | — | — | ND | ND | ND | 0.141 |
| | 2.8 | 0.06 | 0.07 | 0.07 | 0.80 | 0.81 | 0.80 | ND | — | — | ND | ND | ND | 0.14 |
| | 2.9 | 0.06 | 0.06 | 0.05 | 0.67 | 0.66 | 0.66 | ND | — | — | ND | ND | ND | 0.142 |

TABLE 10-continued

| | | | | | | | | | | | | | | |
|---|---|---|---|---|---|---|---|---|---|---|---|---|---|---|
| At | 2.5 | 0.08 | — | — | 0.20 | — | — | 0.072 | — | — | BQL | — | — | 0.105 |
| 2-8° C. | 2.6 | 0.08 | 0.08 | 0.08 | 0.72 | 0.73 | 0.72 | ND | — | — | ND | ND | ND | 0.138 |
| | 2.7 | 0.58 | 0.59 | 0.58 | 0.58 | ND | ND | ND | — | — | ND | ND | ND | 0.141 |
| | 2.8 | 0.06 | 0.07 | 0.07 | 0.48 | 0.49 | 0.48 | ND | — | — | ND | ND | ND | 0.14 |
| | 2.9 | 0.06 | 0.06 | 0.05 | 0.42 | 0.42 | 0.41 | ND | — | — | ND | ND | ND | 0.142 |

| | | Observation at different time points upon storage | | | | | | | | | | |
|---|---|---|---|---|---|---|---|---|---|---|---|---|
| | pH | Single maximum unknown impurity (%) | | | | | Total impurity (%) | | | | | |
| | | Time points (months) | | | | | | | | | | |
| Time | | 0 M | | 1 M | | | 0 M | | | 1 M | | |
| points | | II | III | I | II | III | I | II | III | I | II | III |
| At | 2.5 | — | — | 0.159 | — | — | 0.409 | — | — | 1.067 | — | — |
| (25° C. | 2.6 | 0.125 | 0.121 | 0.155 | 0.154 | 0.151 | 0.227 | 0.214 | 0.21 | 1.708 | 1.69 | 1.721 |
| 60% RH) | 2.7 | 0.153 | 0.141 | 0.145 | 0.148 | 0.189 | 0.381 | 0.393 | 0.311 | 1.365 | 1.344 | 1.46 |
| | 2.8 | 0.133 | 0.145 | 0.173 | 0.129 | 0.133 | 0.277 | 0.209 | 0.299 | 1.214 | 1.162 | 1.149 |
| | 2.9 | 0.131 | 0.14 | 0.137 | 0.132 | 0.139 | 0.272 | 0.283 | 0.195 | 0.939 | 0.919 | 1.048 |
| At | 2.5 | — | — | 0.173 | — | — | 0.409 | — | — | 0.43 | — | — |
| 2-8° C. | 2.6 | 0.125 | 0.121 | 0.107 | 0.122 | 0.114 | 0.227 | 0.214 | 0.21 | 0.923 | 1.022 | 0.93 |
| | 2.7 | 0.153 | 0.141 | 0.116 | 0.109 | 0.111 | 0.381 | 0.393 | 0.311 | 0.863 | 0.866 | 0.786 |
| | 2.8 | 0.133 | 0.145 | 0.11 | 0.135 | 0.135 | 0.277 | 0.209 | 0.299 | 0.679 | 0.731 | 0.731 |
| | 2.9 | 0.131 | 0.14 | 0.126 | 0.124 | 0.117 | 0.272 | 0.283 | 0.195 | 0.673 | 0.664 | 0.636 |

ND: Not Detected;

RH—Relative Humidity;

BQL: Below Quantifiable limit;

NA: Not Available

TABLE 11

| Assay of Cetrorelix acetate eq. to Cetrorelix (%) Storage conditions | | | | | | | | | | |
|---|---|---|---|---|---|---|---|---|---|---|
| | | Initial | | | 2-8° C. 1 M | | | 25° C./60% RH 1 M | | |
| pH | Unfiltered | I | II | III | I | II | III | I | II | III |
| 2.6 | 100.05 | 100.25 | 100.04 | 99.63 | 98.65 | 98.32 | 99.27 | 97 | 97.76 | 97.21 |
| 2.7 | — | 100.75 | 100.4 | 100.66 | 98.69 | 99.22 | 98.78 | 98.36 | 98.22 | 98.55 |
| 2.8 | — | 100.7 | 100.93 | 100.99 | 99.39 | 98.76 | 99.05 | 97.64 | 97.62 | 97.65 |
| 2.9 | — | 97.55 | 97.6 | 97.68 | 98.64 | 98.62 | 98.47 | 96.92 | 96.84 | 96.56 |

We claim:

1. A parenteral dosage form comprising:

a ready-to-inject sterile, stable aqueous solution comprising:

(i) cetrorelix in an amount of 0.25 mg/ml, or a pharmaceutically acceptable salt thereof;

(ii) lactic acid in a concentration sufficient to adjust the pH in the range of 4.0 to 5.0; and (iii) water for injection, wherein the osmolality of the solution is about 250 to about 375 mOsm/kg; and after 6 months of storage at 25 °C and 60% relative humidity, the solution contains an Impurity A, a decapeptide of Formula I in an amount less than 0.5% w/v of cetrorelix base, Formula I

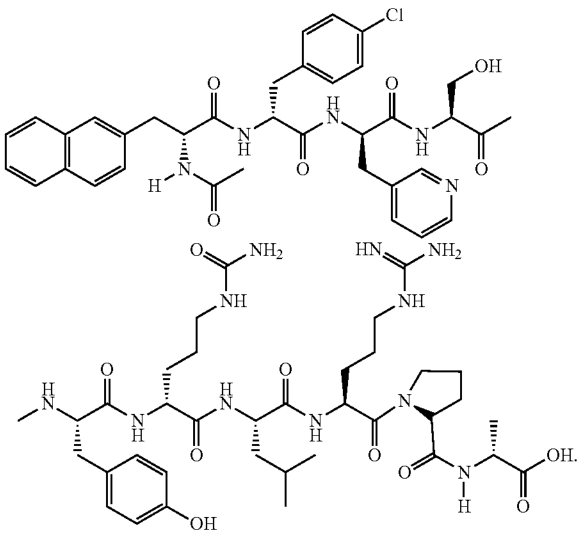

2. The parenteral dosage form according to claim 1, wherein the osmotic agent is present in an amount sufficient for osmolality of the solution in the range 250 to 375 mOsm/Kg.

3. The parenteral dosage form according to claim 2, wherein the ready-to-inject sterile, stable aqueous solutin is present in the resevoir of an injection device.

4. The parenteral dosage form according to claim 3, wherein the injection device is a prefilled syringe.

5. The parenteral dosage form according to claim 3, wherein the injection device is an autoinjector.

6. The parenteral dosage form according to claim 5, wherein the injection device is a pen auto-injector.

7. The parenteral dosage form of claim 1, wherein the aqueous solution is free of one or more of co-solvents, preservatives, and antioxidants.

8. The parenteral dosage form according to claim 2, wherein the injection device is a pen auto-injector.

9. The parenteral dosage form according to claim 1, wherein the parenteral dosage form is suitable for intramuscular use.

10. The parenteral dosage form of claim 1, wherein the osmotic agent is mannitol.

11. The parenteral dosage form according to claim 1, wherein the parenteral dosage form is suitable for subcutaneous use.

12. The parenteral dosage form according to claim 1, wherein the parenteral dosage form is suitable for intramuscular use.

13. The parenteral dosage form of claim 1, wherein the pH of the solution prior to storage is 4.

14. A method of inhibiting premature luteinizing hormone surges in a woman undergoing controlled ovarian stimulation, the method comprising administering a parenteral dosage form according to claim 1 to the woman.

15. The parenteral dosgae form of claim 1, wherein the pH of the solution prior to storage is 5.

16. The parenteral dosage form of claim 1, wherein after 6 months of storage at 25 °C and 60% relative humidity, the solution contains an amount of Impurity A which is from 0.001% to 0.5% by weight of cetrorelix base.

17. The parenteral dosage form of claim 1, wherein the solution comprises cetrorelix acetate.

18. The parenteral dosage form of claim 1, wherein the aqueous solution comprises mannitol.

19. The parenteral dosage form of claim 18, wherein the aqueous solution comprises from about 50.0 to about 58.0 mg/mL mannitol.

20. The parenteral dosage form of claim 1, wherein the solution has a turbidity of less than 2 NTU after 6 months of storage at 25 °C and 60% relative humidity.

* * * * *